(12) United States Patent
Yoo et al.

(10) Patent No.: US 8,366,905 B2
(45) Date of Patent: Feb. 5, 2013

(54) APPARATUS HAVING REDUCED NOISE AND METHOD OF USING THE APPARATUS FOR DETECTING IONIC MATERIALS

(75) Inventors: Kyu-tae Yoo, Yongin-si (KR); Seong-jin Kim, Minneapolis, MN (US); Eui-sik Yoon, Minneapolis, MN (US)

(73) Assignees: Samsung Electronics Co., Ltd. (KR); Regents of the University of Minnesota, Minneapolis, MN (US)

( * ) Notice: Subject to any disclaimer, the term of this patent is extended or adjusted under 35 U.S.C. 154(b) by 318 days.

(21) Appl. No.: 12/850,074

(22) Filed: Aug. 4, 2010

(65) Prior Publication Data

US 2010/0295566 A1    Nov. 25, 2010

Related U.S. Application Data

(62) Division of application No. 11/837,157, filed on Aug. 10, 2007, now Pat. No. 7,824,530.

(30) Foreign Application Priority Data

Dec. 20, 2006 (KR) .................. 10-2006-0130841

(51) Int. Cl.
*G01N 27/26* (2006.01)
*H01L 29/66* (2006.01)

(52) U.S. Cl. ............... 205/777.5; 257/253; 204/403.01; 204/416

(58) Field of Classification Search ............ 204/403.01, 204/416; 205/777.5, 789; 435/6; 257/253
See application file for complete search history.

(56) References Cited

U.S. PATENT DOCUMENTS

| 4,238,757 | A | 12/1980 | Schenck |
|---|---|---|---|
| 4,730,479 | A | 3/1988 | Pyke et al. |
| 4,777,019 | A | 10/1988 | Dandekar |
| 5,827,482 | A | 10/1998 | Shieh et al. |
| 7,824,530 | B2 * | 11/2010 | Yoo et al. ............... 204/403.01 |
| 2004/0134798 | A1 * | 7/2004 | Toumazou et al. ........ 205/793.5 |
| 2005/0017190 | A1 | 1/2005 | Eversmann et al. |
| 2005/0062093 | A1 * | 3/2005 | Sawada et al. ............ 257/316 |
| 2006/0057025 | A1 | 3/2006 | Eversmann et al. |

FOREIGN PATENT DOCUMENTS

| EP | 0 679 720 A1 | 11/1995 |
|---|---|---|
| EP | 1 217 364 A2 | 6/2002 |
| JP | 2002-340853 A | 11/2002 |
| KR | 1993-0002824 B1 | 4/1993 |

OTHER PUBLICATIONS

Extended European Search Report for Application No. 07120776.5-2204/1935990 dated Oct. 27, 2011.
Schaper, et al., Parameter Variation on Chip-Level, Proc. IEEE 2005 Int. Conference on Microelectronic Test Structures, vol. 18, Apr. 2005, pp. 155-158.

* cited by examiner

*Primary Examiner* — Jeffrey T Barton
*Assistant Examiner* — Jennifer Dieterle
(74) *Attorney, Agent, or Firm* — Cantor Colburn LLP

(57) ABSTRACT

An apparatus and method for detecting ionic materials includes a sensing electrode which contacts a liquid sample and detects a sensing voltage corresponding to a surface potential which is changed by a concentration of ionic materials in the liquid sample, a first switching transistor having a first terminal connected to the sensing electrode and a second terminal connected to a first node, a second switching transistor having a first terminal connected to a reset voltage and a second terminal connected to the first node, and a sensing transistor having a gate connected to the first node.

7 Claims, 10 Drawing Sheets

APPARATUS HAVING REDUCED NOISE AND METHOD OF USING THE APPARATUS FOR DETECTING IONIC MATERIALS

This application is a divisional of U.S. application Ser. No. 11/837,157, filed on Aug. 10, 2007, which claims priority to Korean Patent Application No. 10-2006-0130841, filed on Dec. 20, 2006, and all the benefits accruing therefrom under 35 U.S.C. §119, the contents of which in its entirety are herein incorporated by reference.

BACKGROUND OF THE INVENTION

1. Field of the Invention

The present invention relates to an apparatus and method for detecting ionic materials, and more particularly, to an apparatus having reduced noise and a method of using the apparatus for detecting ionic materials.

2. Description of the Related Art

Transistor-based biosensors use electric signals to detect ionic materials such as biomolecules. Transistor-based biosensors are manufactured using a semiconductor formation process, and have an advantage of rapid conversion of sensed signals into electrical signals. Thus, a considerable amount of research has been conducted into manufacturing transistor-based biosensors.

A biosensor for detecting biological reactions using a field effect transistor ("FET") is disclosed in U.S. Pat. No. 4,238,757. According to the biosensor for detecting biological reactions of the prior art in U.S. Pat. No. 4,238,757, a surface charge concentration changes due to an antigen-antibody reaction, thereby affecting a charge concentration in a semiconductor inversion layer. The change in the charge concentration can be detected by measuring a change in current. In the biosensor for detecting biological reactions of the prior art disclosed in U.S. Pat. No. 4,238,757, a protein is used as a biomolecule in the biosensor.

U.S. Pat. No. 4,777,019 discloses a biosensor based on a principle in which biological monomers are adsorbed on a surface of a gate and a degree of hybridization of the biological monomers with their complementary monomers may be measured using a FET to detect a presence of biological molecules.

FIG. 1 is a cross-sectional view of a FET of the prior art for detecting biomolecules. Referring to FIG. 1, a source 12 and a drain 13 are formed in both sides of a substrate 11 doped with an n- or p-type impurity, and each have polarities opposite to a polarity of the substrate 11. A channel 15 is formed between the source 12 and the drain 13, and an insulating layer 14 contacting the source 12 and the drain 13 is formed on the substrate 11. A reference electrode 16 is disposed above the insulating layer 14. A predetermined voltage is applied to the reference electrode 16.

A liquid sample (not shown) containing biomolecules comes into contact with the insulating layer 14 and the reference electrode 16. An amount of current flowing between the source 12 and the drain 13 changes according to a concentration of the biomolecules in the liquid sample, and a concentration of the biomolecules can therefore be obtained by measuring a change in the current flowing between the source 12 and the drain 13.

In the prior art, a concentration of biomolecules is detected using an array of FETs constructed as described above and by using the FET arrays in a plurality of chambers.

In the prior art, individual FETs of the plurality of FETs have different electrical characteristics, caused by a physical variation in device dimensions during a semiconductor manufacturing process, a variation in doping density during the semiconductor manufacturing process, and a variation in threshold voltage due to surface effects on the FETs, such as trapped charges in a gate oxide or surface states.

Further, the deviations of the electrical characteristics of the FETs increase as the FETs decreases in size or the distance between the FETs increases. The different electrical characteristics of the FETs adversely affect performance parameters such as precision, reproducibility and resolution of biomolecule detection.

FIG. 2 is a graph of voltage illustrating deviations of electrical characteristics of FETs constructed as the FET of the prior art in FIG. 1.

Referring to FIG. 2, an array of 45 conventional FETs is disposed in three chambers. More specifically, FETs 1-15 are disposed in Chamber 1, FETs 16-30 are disposed in Chamber 2 and FETs 31-45 are disposed in Chamber 3, as shown in FIG. 2. A voltage of 1.695 V was input to each of the 45 FETs. Although an output voltage of 1.695 V was expected, the output voltages of the conventional FETs were different from one another due to the electrical characteristic differences of the conventional FETs described above. An average output voltage was 1.699 V, a standard deviation was 5 mV, and a difference between a maximum output voltage and a minimum output voltage was 23.7 mV, as shown in FIG. 2. Thus, there is a significant possibility that an error in measurement results may occur due to the electrical characteristic differences of the FETs of the prior art.

BRIEF SUMMARY OF THE INVENTION

The present invention provides an apparatus for detecting ionic materials having significantly reduced noise caused by differences in electrical characteristics between transistors.

The present invention also provides a microfluidic device for detecting ionic materials, having significantly reduced noise caused by differences in electrical characteristics between transistors.

The present invention also provides a method of easily and accurately detecting a presence and concentration of ionic materials.

According to one exemplary embodiment of the present invention, an apparatus for detecting ionic materials includes: a sensing electrode which contacts a liquid sample and detects a sensing voltage corresponding to a surface potential which changes according to a concentration of ionic materials in the liquid sample; a first switching transistor having a first terminal connected to the sensing electrode and a second terminal connected to a first node; a second switching transistor having a first terminal connected to a reset voltage and a second terminal connected to the first node; and a sensing transistor having a gate connected to the first node.

The apparatus may further include a voltage detecting unit connected to the first terminal of the sensing transistor and the second terminal of the sensing transistor and which detects a voltage applied to the gate of the sensing transistor.

The voltage detecting unit may be a voltage follower which outputs a voltage of an input terminal of the voltage detecting unit to an output terminal of the voltage detecting unit.

The apparatus may further include a third switching transistor having a first terminal connected to a second terminal of the sensing transistor.

The apparatus may further include a voltage subtracting unit which calculates a voltage difference between voltages sequentially applied to the gate of the sensing transistor and outputs the calculated voltage difference.

The sensing electrode may be formed of one selected from the group consisting of aluminum (Al), platinum (Pt), gold (Au) and copper (Cu).

According to another exemplary embodiment of the present invention, an apparatus for detecting ionic materials includes: a plurality of sensing electrodes wherein each sensing electrode of the plurality of sensing electrodes contacts a respective liquid sample and detects a respective sensing voltage corresponding to a respective surface potential which is changed by a concentration of ionic materials in the respective liquid sample; a plurality of first switching transistors each having a first terminal connected to a respective sensing electrodes and a second terminal connected to a respective first node of a plurality of first nodes; a plurality of second switching transistors each having a first terminal connected to a reset voltage and a second terminal connected to a respective first node of the plurality of first nodes; a plurality of sensing transistors each having a gate connected to a respective first node of the plurality of first nodes; a plurality of third switching transistors each having a first terminal connected to a second terminals of a respective sensing transistors of the plurality of sensing transistors; and a voltage detecting unit which selectively detects a voltage applied to a gates of a respective sensing transistor of the plurality of sensing transistors in response to a switching operation of a respective third switching transistor of the plurality of third switching transistors.

The voltage detecting unit may be a voltage follower which outputs a voltage of an input terminal of the voltage follower to an output terminal of the voltage follower.

A first terminals of each of the sensing transistors and a second terminal of each of the third switching transistors may be each connected to each other in electrical parallel and comprise a positive input terminal of the voltage follower.

The apparatus may further include a voltage subtracting unit which calculates a voltage difference between voltages sequentially applied to the gates of the sensing transistors and outputs the calculated voltage difference.

The sensing electrodes may be formed of one selected from the group consisting of Al, Pt, Au and Cu.

According to another exemplary embodiment of the present invention, a microfluidic device for detecting ionic materials includes an apparatus for detecting ionic materials.

The apparatus for detecting ionic materials includes: a sensing electrode which contacts a liquid sample and detects a sensing voltage corresponding to a surface potential which changes in accordance with a concentration of ionic materials in the liquid sample; a first switching transistor having a first terminal connected to the sensing electrode and a second terminal connected to a first node; a second switching transistor having a first terminal connected to a reset voltage and a second terminal connected to the first node; and a sensing transistor having a gate connected to the first node.

The sensing electrode of the apparatus may be disposed in a microchannel and contact a liquid sample which flows in the microchannel.

The microfluidic device may further include a reference electrode disposed in the microchannel and which contacts the liquid sample, wherein a predetermined voltage is applied to the reference electrode.

In yet another exemplary embodiment of the present invention, a microfluidic device for detecting ionic materials includes an apparatus for detecting ionic materials.

The apparatus for detecting ionic materials includes: a plurality of sensing electrodes wherein each sensing electrode of the plurality of sensing electrodes contacts a respective liquid sample and detects a respective sensing voltage corresponding to a respective surface potential which is changed by a concentration of ionic materials in the respective liquid sample; a plurality of first switching transistors each having a first terminal connected to a respective sensing electrode of the plurality of sensing electrodes and a second terminal connected to a respective first node of a plurality of first nodes; a plurality of second switching transistors each having a first terminal connected to a reset voltage and a second terminal connected to a respective first node of the plurality of first nodes; a plurality of sensing transistors each having a gate connected to a respective first node of the plurality of first nodes; a plurality of third switching transistors each having a first terminal connected to a second terminal of a respective sensing transistor of the plurality of sensing transistors; and a voltage detecting unit which selectively detects a voltage applied to a gate of a respective sensing transistor of the plurality of sensing transistors in response to a switching operation of a respective third switching transistor of the plurality of third switching transistors.

The sensing electrode of the apparatus may be disposed in a microchannel and contact a liquid sample which flows in the microchannel.

The microfluidic device may further include a reference electrode disposed in the microchannel and which contacts the liquid sample, wherein a predetermined voltage is applied to the reference electrode.

According to still another exemplary embodiment of the present invention, a method of detecting ionic materials includes: detecting a sensing voltage according to a concentration of ionic materials in a liquid sample using a sensing electrode contacting the liquid sample; applying the sensing voltage to a gate of a sensing transistor; measuring a first gate voltage corresponding to the sensing voltage being applied to the gate of the sensing transistor; applying a reset voltage to the gate of the sensing transistor; measuring a second gate voltage corresponding to the reset voltage being applied to the gate of the sensing transistor; and calculating a voltage difference between the first gate voltage the second gate voltage.

The detecting the sensing voltage, the applying the sensing voltage, the measuring the first gate voltage, the measuring the second gate voltage and the calculating the voltage difference between the first gate voltage and the second gate voltage may be performed by sensing transistors configured in an array.

The ionic materials may be biomolecules. The biomolecules may be nucleic acids or proteins.

The nucleic acids may be selected from the group consisting of deoxyribonucleic acids ("DNAs"), ribonucleic acids ("RNAs"), peptide nucleic acids ("PNAs"), locked nucleic acids ("LNAs") and hybrids thereof.

The nucleic acids may be polymerase chain reaction ("PCR") products or extracts thereof.

The proteins may be selected from the group consisting of enzymes, substrates, antigens, antibodies, ligands, aptamers, and receptors.

BRIEF DESCRIPTION OF THE DRAWINGS

The above and other aspects, features and advantages of the present invention will become more readily apparent by describing in further detail exemplary embodiments thereof with reference to the accompanying drawings, in which.

DETAILED DESCRIPTION OF THE INVENTION

Figure 1:
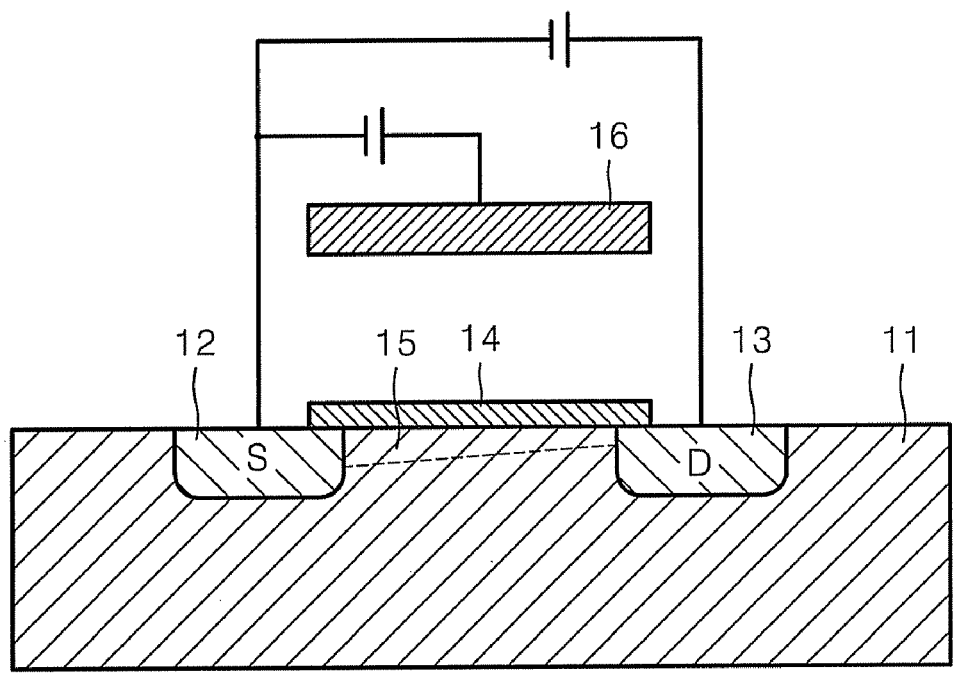
FIG. 1 is a cross-sectional view of a field effect transistor ("FET") of the prior art for detecting biomolecules.

The invention will now be described more fully hereinafter with reference to the accompanying drawings, in which exemplary embodiments of the invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the device in one of the figures were turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning which is consistent with their meaning in the context of the relevant art and the present disclosure, and will not be interpreted in an idealized or overly formal sense unless expressly so defined herein.

Exemplary embodiments of the present invention are described herein with reference to cross section illustrations which are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes which result, for example, from manufacturing. For example, a region illustrated or described as flat may, typically, have rough and/or nonlinear features. Moreover, sharp angles which are illustrated may be rounded. Thus, the regions illustrated in the figures are schematic in nature and their shapes are not intended to illustrate the precise shape of a region and are not intended to limit the scope of the present invention.

The present invention will now be described in further detail with reference to the accompanying drawings.

Figure 3:
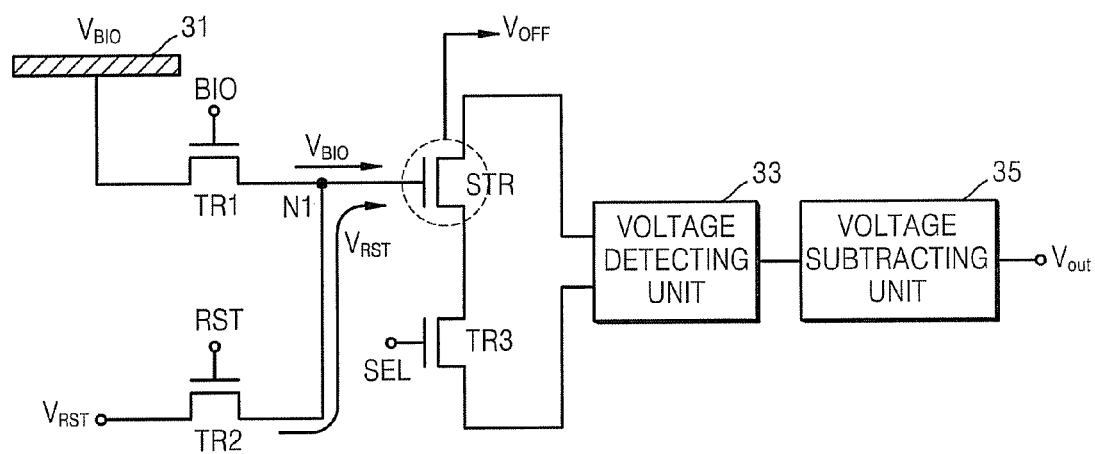
FIG. 3 is a schematic circuit diagram of an apparatus for detecting ionic materials according to an exemplary embodiment of the present invention.

FIG. 3 is a schematic circuit diagram of an apparatus for detecting ionic materials according to an exemplary embodiment of the present invention.

Referring to FIG. 3, the apparatus includes a sensing electrode 31, a first switching transistor TR1, a second switching transistor TR2, a third switching transistor TR3, a sensing transistor STR, a voltage detecting unit 33 and a voltage subtracting unit 35.

The sensing electrode 31 contacts a liquid sample (not shown) and detects a sensing voltage $V_{BIO}$ proportional to a change in a surface potential of the sensing electrode 31 according to a concentration of ionic materials contained in the liquid sample. The sensing electrode 31 may be formed of aluminum (Al), platinum (Pt), gold (Au) or copper (Cu), for example, but is not limited thereto.

The first switching transistor TR1 has a first terminal connected to the sensing electrode 31 and a second terminal connected to a first node N1. The first switching transistor TR1 transmits the sensing voltage $V_{BIO}$ to the first node N1 using a sensing select signal BIO applied to a gate of the first switching transistor TR1.

The second switching transistor TR2 has a first terminal connected to a reset voltage $V_{RST}$ and a second terminal connected to the first node N1. The second switching transistor TR2 transmits the reset voltage $V_{RST}$ to the first node N1 according to a reset select signal RST which is applied to a gate of the second switching transistor TR2.

The sensing transistor STR has a gate connected to the first node N1, a first terminal connected to the voltage detecting unit 33, and a second terminal connected to a first terminal of the third transistor TR3.

The sensing voltage $V_{BIO}$ or the reset voltage $V_{RST}$ is selectively applied to the gate of the sensing transistor STR by the first switching transistor TR1 or the second switching transistor TR2, respectively.

The third switching transistor TR3 has the first terminal connected to the second terminal of the sensing transistor STR and a second terminal connected to the voltage detecting unit 33. The third switching transistor TR3 connects the sensing transistor STR to the voltage detecting unit 33 using a select signal SEL which is applied to a gate of the third switching transistor TR3.

Further referring to FIG. 3, the voltage detecting unit 33 is connected to the first terminal of the sensing transistor STR and the second terminal of the third switching transistor TR3. The voltage detecting unit 33 detects a voltage which is applied to the gate of the sensing transistor STR. For example, the voltage detecting unit 33 may detect a change in a voltage which is applied to the gate of the sensing transistor STR based on a change in current flowing between the first terminal and the second terminal of the sensing transistor STR.

In an exemplary embodiment, the voltage detecting unit 33 may be a voltage follower which outputs a voltage of an input terminal of the voltage detecting unit 33 (not specifically labeled in FIG. 3) to an output terminal of the voltage detecting unit 33 (not specifically labeled in FIG. 3). Further, the sensing transistor STR and the third switching transistor TR3 may be connected to or constitute a positive input terminal of the voltage follower, for example, but are not limited thereto in alternative exemplary embodiments of the present invention.

The voltage subtracting unit 35 calculates a voltage difference between voltages which are sequentially applied to the gate of the sensing transistor STR and outputs the calculated voltage difference as an output voltage Vout.

The operation of the apparatus for detecting ionic materials according to an exemplary embodiment of the present invention will now be explained in further detail with reference to FIG. 3.

As described above, deviations in electrical characteristics of transistors are caused by a physical variation in device dimensions during a manufacturing process, a variation in doping density and a variation in threshold voltage. As a result of the deviations in electrical characteristics, different signals are output even though the same signal is input.

For example, each transistor has its own noise factor corresponding to a difference between an output signal and an input signal. In FIG. 3, a noise of the sensing transistor STR is modeled as a noise voltage $V_{OFF}$.

The liquid sample containing the ionic materials contacts the sensing electrode 31 and the first switching transistor TR1 is turned on while the second switching transistor TR2 is turned off to apply the sensing voltage $V_{BIO}$ detected by the sensing electrode 31 to the gate of the sensing transistor STR.

The voltage detecting unit 33 measures the voltage applied to the gate of the sensing transistor STR. Even though it is preferable that only the sensing voltage $V_{BIO}$ is measured by the voltage detecting unit 33, the noise $V_{OFF}$ of the sensing transistor STR is added to the sensing voltage $V_{BIO}$ and thus a sensing output voltage $V_{BIO}+V_{OFF}$ is actually measured by the voltage detecting unit 33.

Next, the first switching transistor TR1 is turned off and the second switching transistor TR2 is turned on to apply the reset voltage $V_{RST}$ to the gate of the sensing transistor STR.

The voltage detecting unit 33 then measures the voltage applied to the gate of the sensing transistor STR. As above, even though it is preferable that only the reset voltage $V_{RST}$ is measured by the voltage detecting unit 33, the noise $V_{OFF}$ of the sensing transistor STR is added to the reset voltage $V_{RST}$ and thus a reset output voltage $V_{RST}+V_{OFF}$ is actually measured by the voltage detecting unit 33.

To compensate for the noise voltage $V_{OFF}$, the voltage subtracting unit 35 outputs a differential voltage $V_{BIO}-V_{RST}$ between the sensing output voltage $V_{BIO}+V_{OFF}$ and the reset output voltage $V_{RST}+V_{OFF}$ as an output voltage $V_{out}$. Thus, the noise $V_{OFF}$ of the sensing transistor STR is not included in the output voltage $V_{out}$. Accordingly, the apparatus according to an exemplary embodiment of the present invention provides an improved detection performance, e.g., the noise $V_{OFF}$ of the sensing transistor STR is removed from the output voltage $V_{out}$.

Since the reset voltage $V_{RST}$ is known, the sensing voltage $V_{BIO}$ can be obtained by adding the reset voltage $V_{RST}$ to the differential voltage $V_{BIO}-V_{RST}$. The addition of the reset voltage $V_{RST}$ to the differential voltage $V_{BIO}-V_{RST}$ may be performed by the voltage subtracting unit 35, for example, or may be performed by other elements in alternative exemplary embodiments of the present invention.

Figure 4:
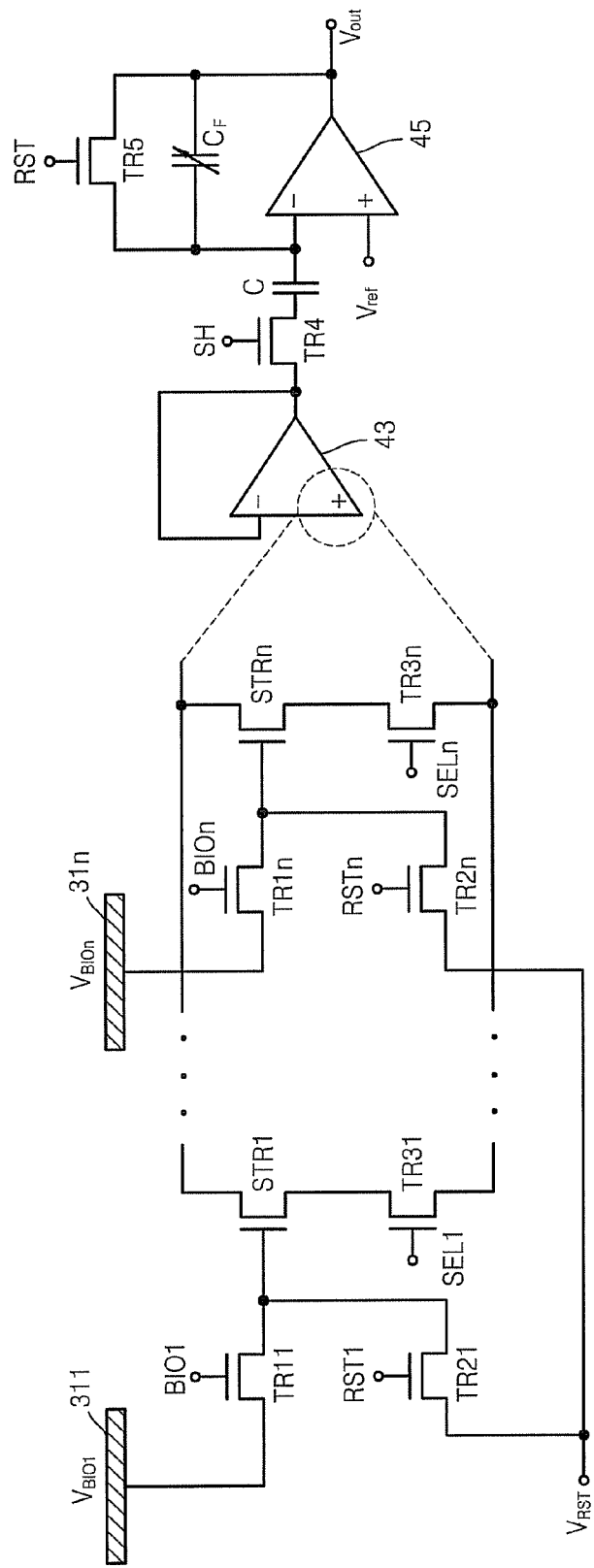
FIG. 4 is a schematic circuit diagram of an apparatus for detecting ionic materials according to an alternative exemplary embodiment of the present invention.

FIG. 4 is a circuit diagram of an apparatus for detecting ionic materials according to an alternative exemplary embodiment of the present invention.

The following explanation will be made focusing on differences between the apparatus of FIG. 3 and the apparatus of FIG. 4. Further, the same reference numerals designate the same or like components in FIGS. 3 and 4, and repetitive descriptions of components of the apparatus in FIG. 4 having the same or like descriptions as components in the apparatus of FIG. 3 have been omitted below.

Referring to FIG. 4, the apparatus for detecting ionic materials includes n sensing electrodes 311 through 31$n$, n first switching transistors TR11 through TR1$n$, n second switching transistors TR21 through TR2$n$, n third switching transistors TR31 through TR3$n$ and n sensing transistors STR1 through STRn. Each of the n sensing electrodes 311 through 31$n$, n first switching transistors TR11 through TR1$n$, n second switching transistors TR21 through TR2$n$, n third switching transistors TR31 through TR3$n$ and n sensing transistors STR1 through STRn is configured as in FIG. 3, except that first terminals of the sensing transistors STR1 through STRn are connected in electrical parallel with each other, and second terminals of the third switching transistors TR31 through TR3n are connected in electrical parallel with each other, as shown in FIG. 4.

Further, the n sensing electrodes 311 through 311n contact a liquid sample (not shown) and detect sensing voltages $V_{BIO1}$ through $V_{BIOn}$, the n first switching transistors TR11 through TR1n use sensing select signals BIO1 through BIOn to transmit the sensing voltages $V_{BIO1}$ through $V_{BIOn}$ to n sensing transistors STR1 through STRn, the n second switching transistors TR21 through TR2n receive reset select signals RST1 through RSTn and the n third switching transistors TR31 through TR3n receive select signals SEL1 through SELn, in a similar manner as described above in greater detail with reference to FIG. 3.

In an exemplary embodiment, an array of the n sensing electrodes 311 through 31n may be disposed in one chamber or microchannel of a microfluidic device. In an alternative exemplary embodiment, the n sensing electrodes 311 through 31n may be divided into arrays and disposed in a plurality of chambers or microchannels of the microfluidic device.

The sensing transistors STR1 through STRn and the third switching transistors TR31 through TR3n may be connected to or constitute a positive input terminal of a voltage follower 43 which functions as a voltage detecting unit as described in greater detail above.

In the voltage follower 43, the third switching transistors TR31 through TR3n are selectively switched on to connect one of the sensing transistors STR1 through STRn to the positive input terminal of the voltage follower 43, and thus the voltage follower 43 detects voltages applied to gates of the sensing transistors STR1 and STRn.

A reset voltage $V_{RST}$ is commonly applied to first terminals of the second switching transistors TR21 through TR2n.

The voltage follower 43 is connected to a variable gain amplifier 45 through a fourth switching transistor TR4 gated by an output select signal SH.

The variable gain amplifier 45 calculates a voltage difference between a sensing output voltage $V_{BIO}+V_{OFF}$ and a reset output voltage $V_{RST}+V_{OFF}$ and may amplify the calculated voltage difference.

A capacitor C is connected between a negative input terminal of the variable gain amplifier 45 and the fourth switching transistor TR4, and a reference voltage $V_{ref}$ is applied to a positive input terminal of the variable gain amplifier 45. A variable capacitor $C_F$ and a fifth switching transistor TR5 are connected in electrical parallel with each other between the negative input terminal and an output terminal of the variable gain amplifier 45. A configuration of the variable gain amplifier 45 may be modified in alternative exemplary embodiments of the present invention.

A voltage $V_{out}$ output from one of the sensing transistors STR1 through STRn and selected by one of the third switching transistors TR31 through TR3n, the voltage follower 43, and the variable gain amplifier 45 is given by Equation 1.

$$V_{out} = V_{ref} - C/C_F \times [(V_{BIO}+V_{OFF}) - (V_{RST}+V_{OFF})] = V_{ref} - C/C_F \times (V_{BIO} - V_{RST}) \quad (1)$$

Since values of the capacitor C, the variable capacitor, $C_F$, the reference voltage $V_{ref}$ and the reset voltage $V_{RST}$ are known, a value of the sensing voltage $V_{BIO}$ can be determined according to Equation 1. Therefore, the apparatus for detecting ionic materials according to an exemplary embodiment of the present embodiment provides a high detection performance without noise from the sensing transistors STR1 through STRn.

Figure 5:
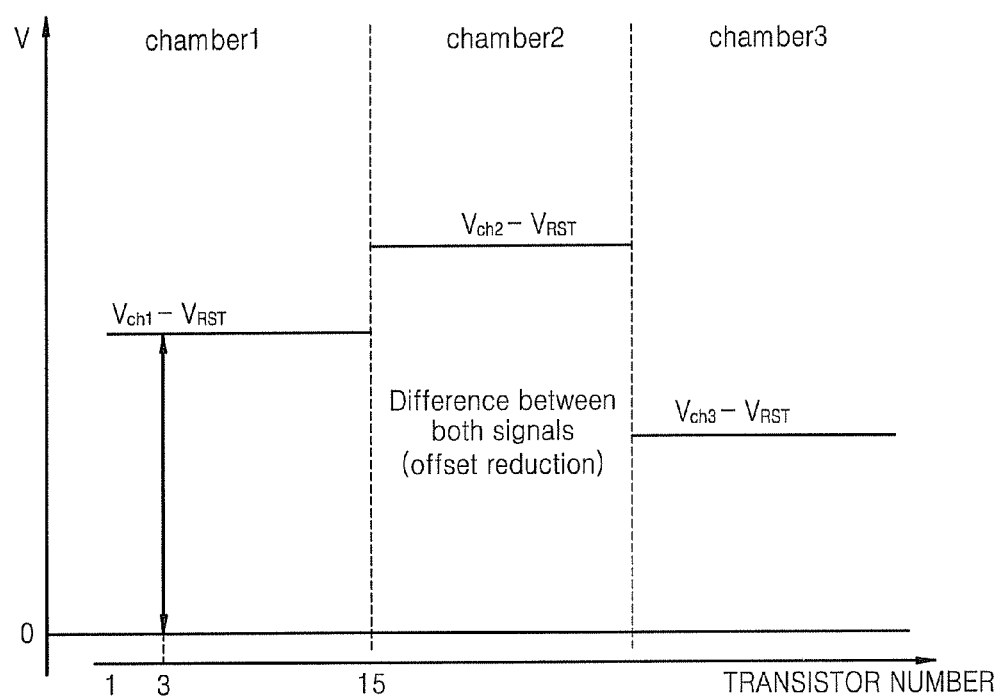
FIG. 5 is a graph of expected voltages illustrating a sensing voltage, a reset voltage and a difference therebetween output from an apparatus for detecting ionic materials according to an exemplary embodiment of the present invention.

FIG. 5 is a graph of expected voltages illustrating a sensing voltage, a reset voltage and a difference therebetween output from an apparatus for detecting ionic materials according to an exemplary embodiment of the present invention.

In FIG. 5, a vertical axis represents a voltage, and a horizontal axis represents sensing transistors in arrays of apparatuses for detecting ionic materials. For example, the array of the plurality of ionic material detecting apparatuses may be disposed in each of three chambers, and liquid samples having different concentrations flow into and out of the three chambers to measure respective voltage changes. Therefore, three different channel sensing voltages $V_{ch1}$, $V_{ch2}$ and $V_{ch3}$ are applied to respective channels, and the same reset voltage $V_{RST}$ is applied to each of the three channels.

A noise voltage $V_{OFF}$ added during a measuring of each of the channel sensing voltages $V_{ch1}$, $V_{ch2}$ and $V_{ch3}$ and the reset voltage $V_{RST}$ are the same for one sensing transistor but are different for different sensing transistors, as described above in greater detail.

Accordingly, by subtracting a reset output voltage $V_{RST}+V_{OFF}$ resulting from the application of the reset voltage $V_{RST}$ from each of sensing output voltages $V_{ch1}+V_{OFF}$, $V_{ch2}+V_{OFF}$, and $V_{ch3}+V_{OFF}$ from the channel sensing voltages $V_{ch1}$, $V_{ch2}$ and $V_{ch3}$, respectively, output signals without the noise voltage $V_{OFF}$ are obtained. Accordingly, inaccurate outputs due to deviations in electrical characteristics between individual sensing transistors of the plurality of sensing transistors are effectively reduced or eliminated.

Figure 6:
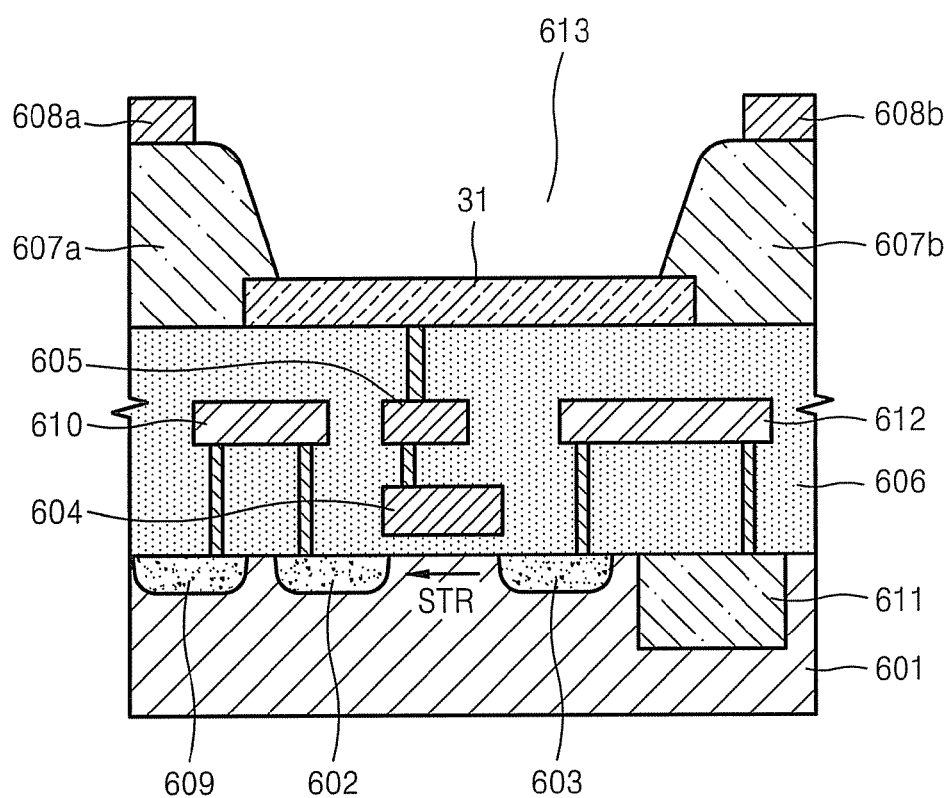
FIG. 6 is a cross-sectional view of a channel and sidewalls defining the channel in a microfluidic device according to an exemplary embodiment of the present invention.

FIG. 6 is a cross-sectional view of a channel and sidewalls defining the channel in a microfluidic device according to an exemplary embodiment of the present invention.

Referring to FIG. 6, the microfluidic device includes a sensing electrode 31, a reference electrodes 608a, a reference electrode 608b and a sensing transistor STR.

The sensing electrode 31 and the reference electrodes 608a and 608b are formed in a microchannel 613 wherein a liquid sample flows. In alternative exemplary embodiments, the reference electrodes 608a and 608b may be formed in a microchamber, for example, but are not limited thereto.

The sensing transistor STR has a first terminal 603, a second terminal 602, and a gate 604. The first terminal 603 is connected to a sensing circuit 611 through a first connecting unit 612, the second terminal 602 is connected to a fourth connecting unit 609 through a second connecting unit 610, and the gate 604 is connected to the sensing electrode 31 through a third connecting unit 605.

The first terminal 603, the second terminal 602, the sensing circuit 611 and the fourth connecting unit 609 are formed in a substrate 601. The gate 604, the first connecting unit 612, the second connecting unit 610 and the third connecting unit 605 are formed in an intermediate layer 606. A passivation layer 607a and a passivation layer 607b cover portions of a surface of the intermediate layer 606 other than the sensing electrode 31, as shown in FIG. 6, to protect the microfluidic device from the liquid sample.

A first switching transistor TR1 (FIG. 3) and a second switching transistor TR2 (FIG. 3) may be connected to the third connecting unit 605. A third switching transistor TR4 (FIG. 3) or the sensing circuit 611 may be connected to the fourth connecting unit 609.

In the microfluidic device for detecting ionic materials according to an exemplary embodiment, an inlet (not shown), an outlet (not shown) and a reaction chamber (not shown), for example, but not being limited thereto, may be fluidly connected to each other through the microchannel 613. In addition to the microchannel 613, the microfluidic device may include a micropump (not shown) which pumps fluids, a microvalve (not shown) which controls a flow of the fluids, a micromixer (not shown) which mixes the fluids and a microfilter (not shown) which filters the fluids, for example, but is not limited thereto.

The microfluidic device further includes a plurality of chambers (not shown) which perform cell counting, cell sorting, deoxyribonucleic acid ("DNA") extraction, polymerase chain reaction ("PCR") amplification and PCR detection for biological assay, for example, but are not limited thereto. The chambers are fluidly connected in a substantially sequential manner by the channels.

Figure 7:
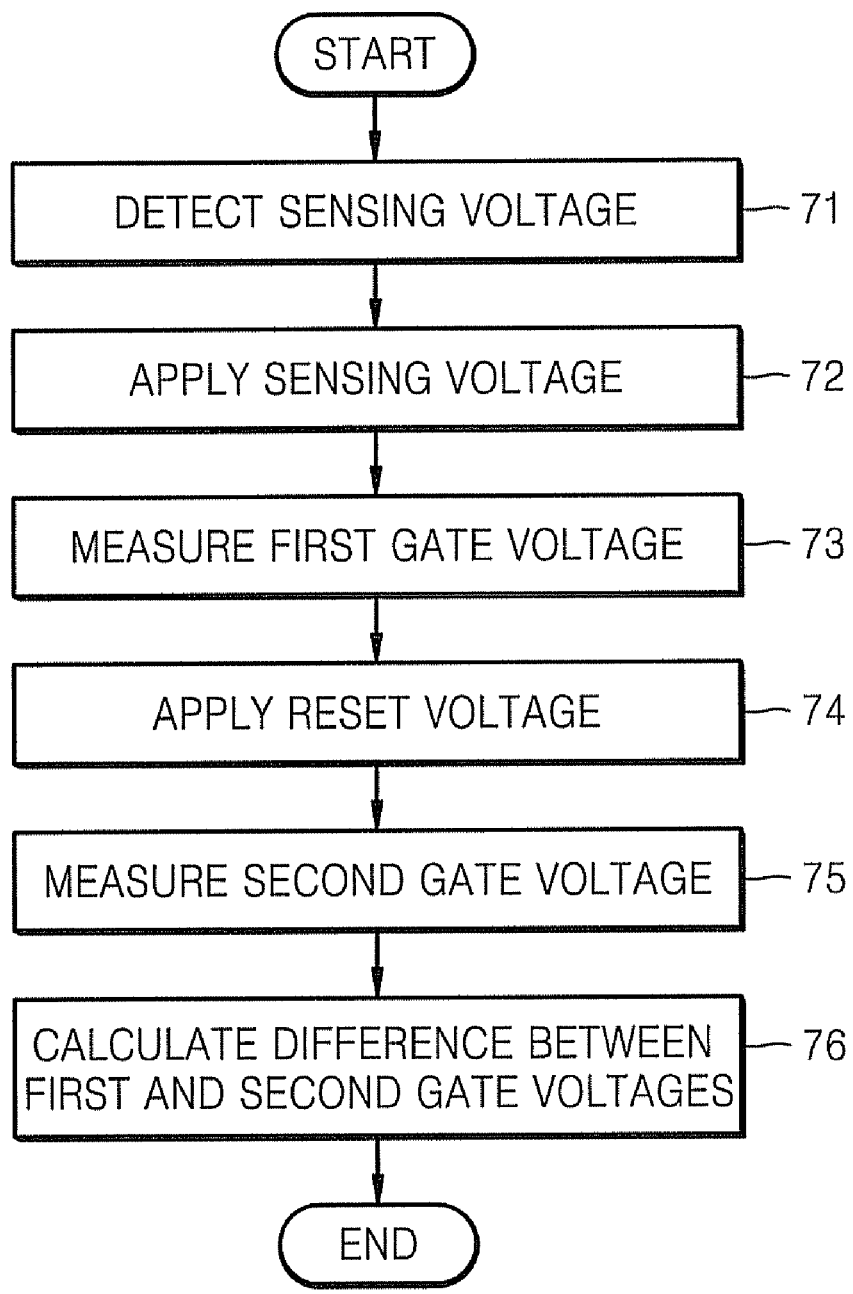
FIG. 7 is a flowchart illustrating a method of detecting ionic materials according to an exemplary embodiment of the present invention.

FIG. 7 is a flowchart illustrating a method of detecting ionic materials according to an exemplary embodiment of the present invention.

Referring to FIG. 7, in operation 71 a sensing voltage is detected according to a concentration of ionic materials contained in a liquid sample using a sensing electrode contacting the liquid sample.

In operation 72, the sensing voltage is applied to a gate of a sensing transistor. In operation 73, a first gate voltage corresponding to when the sensing voltage is applied to the gate of the sensing transistor is measured.

In operation 74, a reset voltage is applied to the gate of the sensing transistor. In operation 75, a second gate voltage corresponding to when the reset voltage is applied to the gate of the sensing transistor is measured.

In operation 76, a difference between the first gate voltage and the second gate voltage is calculated.

According to exemplary embodiments of the present embodiment, signals proportional to a concentration of ionic materials are accurately detected by removing a noise of a sensing transistor.

In alternative exemplary embodiments, the above operations may be performed by a plurality of sensing transistors. In this case, deviations in electrical characteristics of the plurality of sensing transistors is substantially reduced or effectively eliminated.

In exemplary embodiments of the present invention, the ionic materials are any materials containing ions. For example, the ionic materials may be biomolecules, nucleic acids or proteins, for example, but are not limited thereto.

The biomolecules may be nucleic acids or proteins, for example, but are not limited thereto.

The nucleic acids may be selected from the group consisting of DNAs, ribonucleic acids ("RNAs"), peptide nucleic acids ("PNAs"), locked nucleic acids ("LNAs") and hybrids thereof, and PCR products or extracts of the PCR products.

The proteins may be selected from the group consisting of enzymes, substrates, antigens, antibodies, ligands, aptamers and receptors.

Experiments performed on an exemplary embodiment of the present invention will now be described with reference to FIGS. 8-12

Four apparatuses for detecting ionic materials configured as described above in reference to FIG. 4 and including 3 chambers, each chamber containing 15 sensing electrodes, were manufactured by a semiconductor manufacturing process. Each of the 45 total sensing electrodes were connected to first through third switching transistors and a sensing transistor, and the 45 sensing transistors were connected to one voltage follower and one variable gain amplifier.

In Experiment 1, deviations in electrical characteristics of the sensing transistors according to present invention were measured.

In addition, a sensing voltage was applied to apparatuses for detecting ionic materials of the prior art, and deviations thereof were measured. In the apparatuses manufactured according to an exemplary embodiment of the present invention for Experiment 1, however, both a sensing voltage and a reset voltage were applied according to an operation of the first and second switching transistors, the reset voltage was subtracted from the sensing voltage to obtain a differential voltage and the reset voltage was added to the differential voltage output voltage to detect the sensing voltage, as described above in greater detail. Instead of voltages detected by sensing electrodes, a test sensing voltage of 1.695 V was applied as a sensing voltage.

Figure 2:
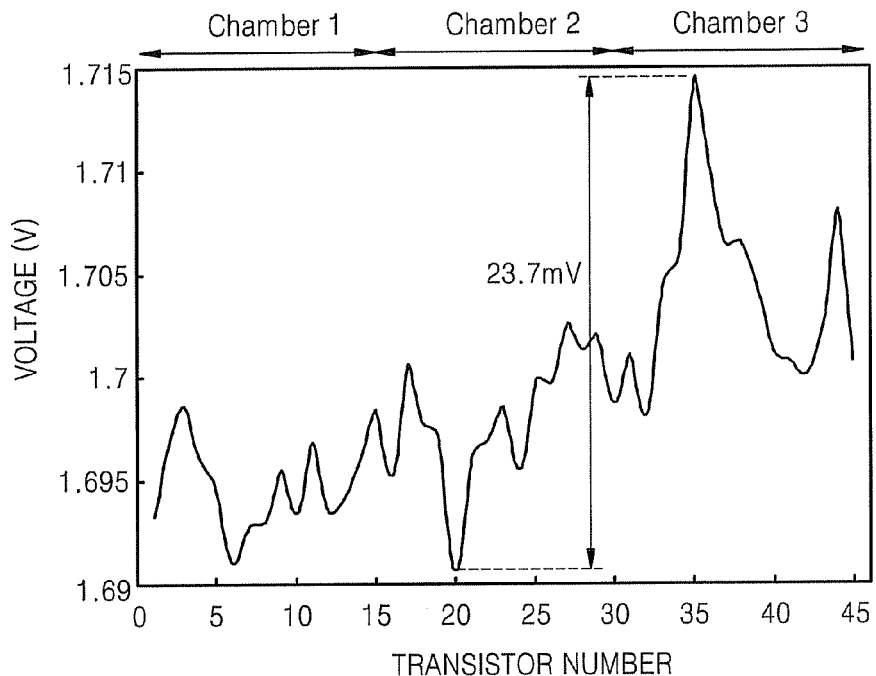
FIG. 2 is a graph of voltages illustrating deviations of electrical characteristics of FETs constructed as the FET of the prior art in FIG. 1.
Figure 8:
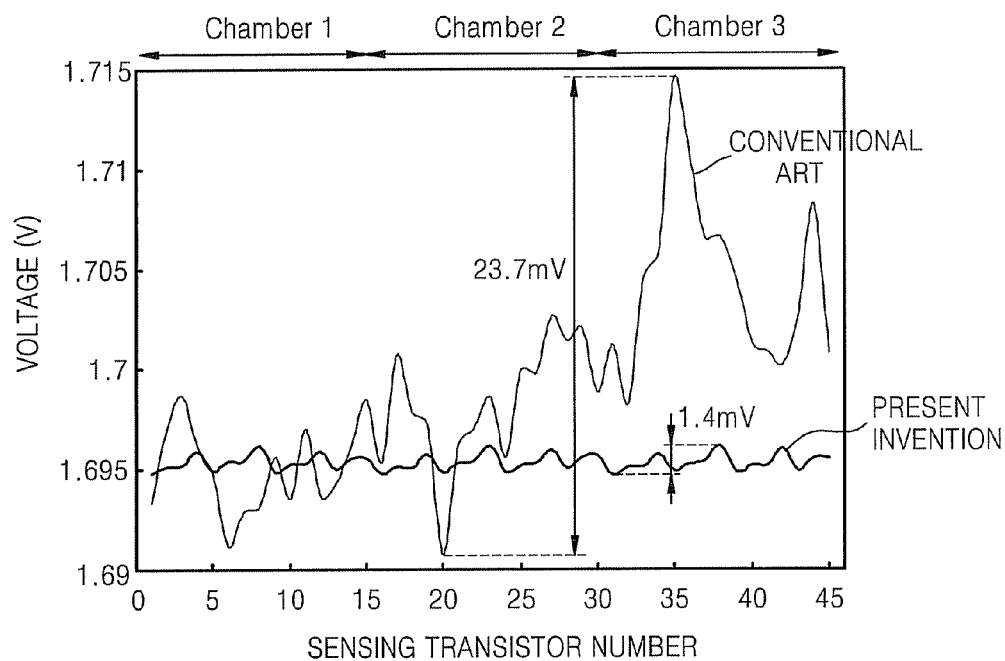
FIG. 8 is a graph of voltages illustrating comparative results between deviations in electrical characteristics between sensing transistors of the apparatus for detecting ionic materials according to the exemplary embodiment of the present invention in FIG. 4 and the deviations in the electrical characteristics of the conventional apparatus of FIG. 2.

FIG. 8 is a graph of voltages illustrating comparative results between deviations in electrical characteristics of the sensing transistors of the apparatus for detecting ionic materials according to the exemplary embodiment of the present invention in FIG. 4 and deviations of electrical characteristics in an apparatus for detecting ionic materials of the prior art in FIG. 2. In FIG. 8, a horizontal axis represents transistor numbers of the sensing transistors contained in respective chambers, and a vertical axis represents a voltage.

Referring to FIG. 8, in the apparatus of the prior art in FIG. 2, an average output voltage was 1.699 V, a standard deviation was 5 mV, and a difference between the maximum voltage and the minimum voltage was 23.7 mV. In contrast, in the apparatus according to an exemplary embodiment of the present invention in FIG. 4, an average output voltage was 1.695 V, a standard deviation was 0.4 mV, and a difference between the maximum voltage and the minimum voltage was 1.4 mV.

Thus, as shown in FIG. 8, the apparatus according to an exemplary embodiment of the present invention, noise and deviations due to differing electrical characteristics between transistors was substantially reduced or effectively eliminated.

In Experiment 2, detection of a PCR product using an apparatus for detecting ionic materials according to an exemplary embodiment of the present invention was tested.

Figure 9:
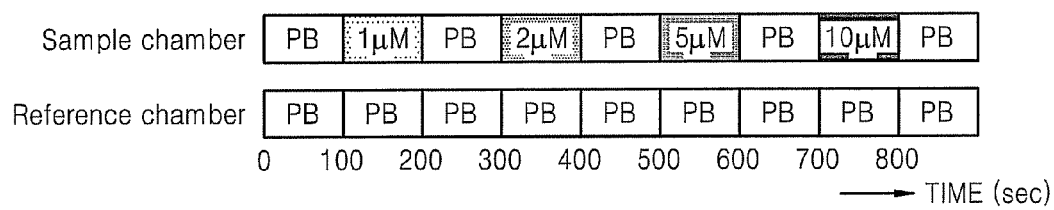
FIG. 9 is a representation of an injection sequence in which a polymerase chain reaction ("PCR") product and a washing buffer were alternately injected to a sample chamber and a reference chamber of the apparatus for detecting ionic materials according to the exemplary embodiment of the present invention in FIG. 4.

FIG. 9 is a representation of an injection sequence in which a PCR product and a washing buffer were alternately injected into the sample chamber and the reference chamber of the apparatus for detecting ionic materials according to the exemplary embodiment of the present invention in FIG. 4.

An investigation was conducted to determine whether a PCR product would be detected without fixing the PCR product to surfaces of the sensing electrodes using the apparatus manufactured for Experiment 1 and whether another PCR product could be effectively detected using the apparatus manufactured FOR Experiment 1 after washing the detected PCR product.

A solution containing a PCR product and a washing solution were alternately injected into the first chamber (sample chamber) of the apparatus, whereas a washing solution was continuously injected into the second chamber (reference chamber). The reference chamber was used to measure a change in a voltage based on a pressure in the reference chamber when the solution was injected.

Referring to FIG. 9, a washing solution PB, a 1 μM PCR product solution, a washing solution PB, a 2 μM PCR product solution, a washing solution PB, a 5 μM PCR production solution, a washing solution PB, a 10 μM PCR product solution and a washing solution PB were sequentially injected in the above order into the sample chamber at 100 second intervals. A washing solution PB was injected into the reference chamber every 100 seconds.

0.01 mM phosphate buffer (pH 6.04) was used as the washing solution. The PCR product had a size of 19 bp.

Figure 10:
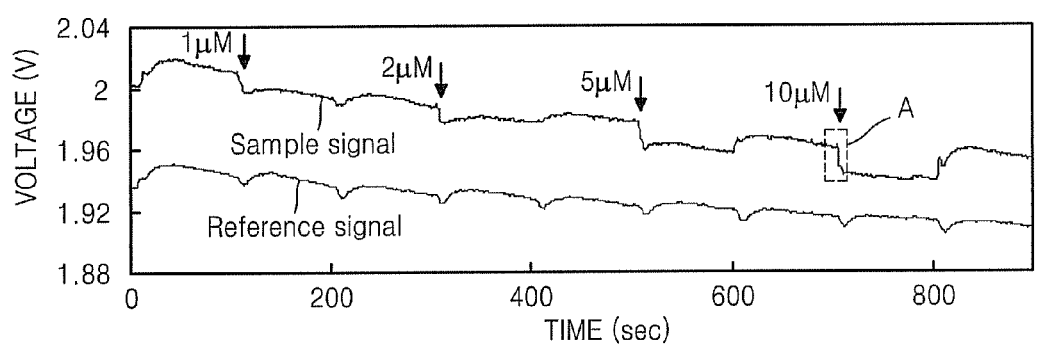
FIG. 10 is a graph of voltage versus time illustrating voltage signals output when the PCR product and the washing buffer were injected in the injection sequence of FIG. 9.
Figure 11:
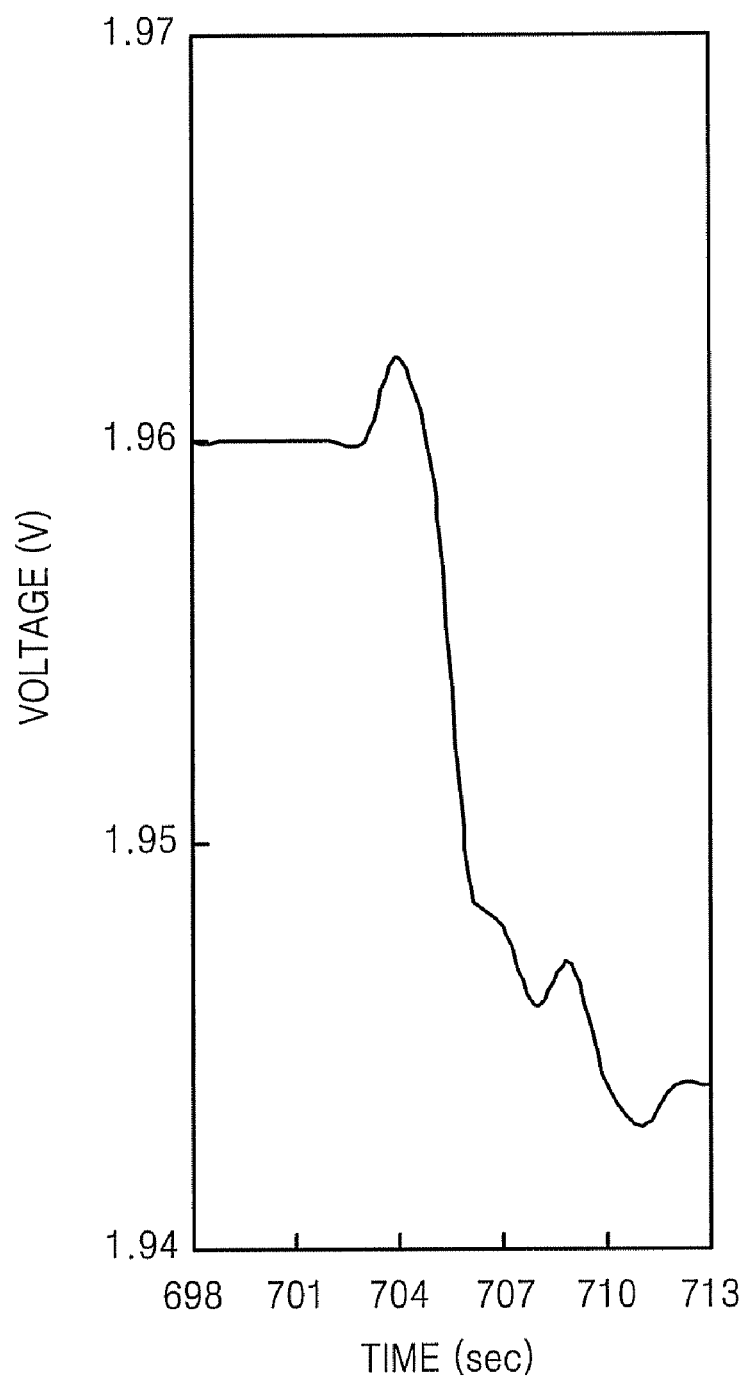
FIG. 11 is an enlarged view of an area A of the graph of voltage versus time in FIG. 10.
Figure 12:
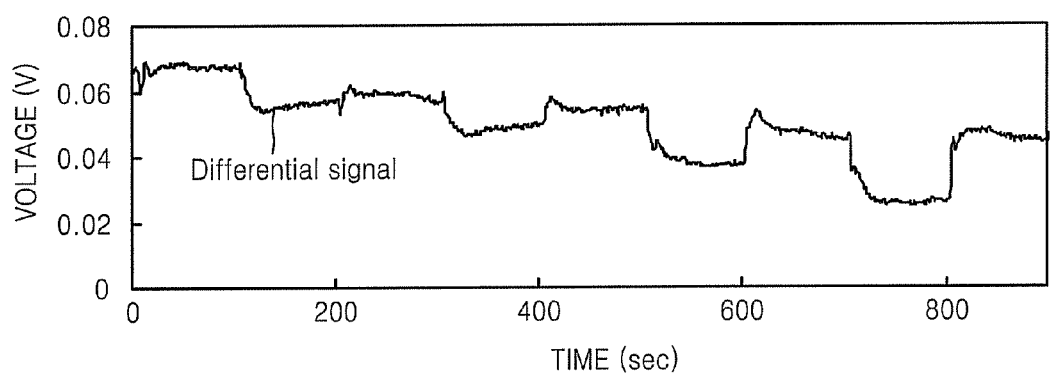
FIG. 12 is a graph of voltage versus time illustrating a differential signal obtained by subtracting the reference signal from the sample signal of the graph of voltage versus time in FIG. 10.

FIG. 10 is a graph of voltage versus time illustrating voltage signals output when the PCR product and the washing buffer were injected in the injection sequence of FIG. 9. FIG. 11 is an enlarged view of an area A of the graph of voltage versus time in FIG. 10. FIG. 12 is a graph of voltage versus time illustrating a differential signal obtained by subtracting the reference signal from the sample signal of the graph of voltage versus time in FIG. 10. The voltage shown in FIGS. 10 through 12 is an average voltage of the 15 sensing transistors included in each chamber.

Referring to FIGS. 10 and 11, when the PCR product was injected, current was reduced sharply. Also, a change in current based on a pressure upon injection of the solution took place.

Referring to FIG. 12, a more accurate result is obtained by subtracting the reference signal from the sample signal.

Hence, a plurality of biomolecules can be easily and accurately detected without fixing the biomolecules using the apparatus for detecting the ionic materials according to exemplary embodiments of the present invention.

As described above, according to exemplary embodiments of the present invention, electrical characteristic differences between transistors can be significantly reduced and noise can thereby be significantly reduced or effectively eliminated. Therefore, ionic materials can be easily and accurately detected using the apparatus for detecting ionic materials and the microfluidic device according to the present invention. Furthermore, if transistors for detecting ionic materials are reduced in size and a distance between the transistors is increased in a multi-chamber structure, the present invention can further provide enhanced advantages.

The present invention should not be construed as being limited to the exemplary embodiments set forth herein. Rather, these exemplary embodiments are provided so that this disclosure will be thorough and complete and will fully convey the concept of the present invention to those skilled in the art.

Further, while the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting ionic materials, the method comprising:

detecting a sensing voltage according to a concentration of ionic materials in a liquid sample using a sensing electrode of an apparatus, the apparatus comprising a first switching transistor having a first terminal connected to the sensing electrode and a second terminal connected to a first node; a second switching transistor having a first terminal connected to a reset voltage and a second terminal connected to the first node; and a sensing transistor having a gate connected to the first node; and the sensing electrode contacting the liquid sample;

applying the sensing voltage to the gate of the sensing transistor;

measuring a first gate voltage corresponding to the sensing voltage being applied to the gate of the sensing transistor;

applying a reset voltage to the gate of the sensing transistor;

measuring a second gate voltage corresponding to the reset voltage being applied to the gate of the sensing transistor; and calculating a voltage difference between the first gate voltage and the second gate voltage.

2. The method of claim 1, wherein the detecting the sensing voltage, the applying the sensing voltage, the measuring the first gate voltage, the measuring the second gate voltage and the calculating the voltage difference between the first gate voltage and the second gate voltage are performed by sensing transistors configured in an array.

3. The method of claim 1, wherein the ionic materials are biomolecules.

4. The method of claim 3, wherein the biomolecules are nucleic acids or proteins.

5. The method of claim 4, wherein the nucleic acids are selected from the group consisting of deoxyribonucleic acids (DNAs), ribonucleic acids (RNAs), peptide nucleic acids (PNAs), locked nucleic acids (LNAs) and hybrids thereof.

6. The method of claim 4, wherein the proteins are selected from the group consisting of enzymes, substrates, antigens, antibodies, ligands, aptamers and receptors.

7. The method of claim 4, wherein the nucleic acids are polymerase chain reaction (PCR) products or extracts thereof.

* * * * *